(12) United States Patent
Miyashita

(10) Patent No.: US 8,481,774 B2
(45) Date of Patent: Jul. 9, 2013

(54) METHOD FOR PRODUCING TETRAFLUORO COMPOUND

(75) Inventor: Yasuhiro Miyashita, Odawara (JP)

(73) Assignee: Nippon Soda Co., Ltd., Tokyo (JP)

( * ) Notice: Subject to any disclaimer, the term of this patent is extended or adjusted under 35 U.S.C. 154(b) by 167 days.

(21) Appl. No.: 13/121,267

(22) PCT Filed: Oct. 2, 2009

(86) PCT No.: PCT/JP2009/005130
§ 371 (c)(1),
(2), (4) Date: Mar. 28, 2011

(87) PCT Pub. No.: WO2010/041402
PCT Pub. Date: Apr. 15, 2010

(65) Prior Publication Data
US 2011/0178323 A1  Jul. 21, 2011

(30) Foreign Application Priority Data

Oct. 7, 2008  (JP) .................................. 2008-260485

(51) Int. Cl.
*C07F 7/08* (2006.01)
*C07C 69/96* (2006.01)
*C07C 43/00* (2006.01)

(52) U.S. Cl.
USPC ........... 556/431; 558/265; 570/134; 570/232; 568/615; 568/842

(58) Field of Classification Search
USPC ... 556/431; 568/615, 842; 558/265; 570/134, 570/232
See application file for complete search history.

(56) References Cited

U.S. PATENT DOCUMENTS

| 4,474,700 A | 10/1984 | Krepan |
| 2005/0043292 A1 | 2/2005 | Parker et al. |

FOREIGN PATENT DOCUMENTS

| WO | WO 03/101449 A2 | 12/2003 |
| WO | WO 2005/019168 A2 | 3/2005 |

OTHER PUBLICATIONS

Gatenyo et al., Journal of Fluorine Chemistry, vol. 130, pp. 332-335 (2009).*
Merritt et al., "The Polar Addition of Molecular Fluorine to Acetylenes," The Journal of Organic Chemistry, vol. 32, 1967, pp. 4124-4126.
"Protective Groups in Organic Synthesis," 1999, pp. 708-715.
Chaudhry et al., "Lithium Aluminum Hydride Reduction of Poly(fluoro-cyclic imides)," Journal of the Chemical Society, 1964, pp. 874-876.
Jikken Kagaku Koza, 5th Edition, vol. 13, 2004, pp. 357-363. (with English-language translation).
Shin Jikken Kagaku Koza, vol. 14, 1979, pp. 325-331. (with English-language translation).
Rapp et al., "Reactions of Polyfluoro Olefins. I. Preparing of Sulfides and Sulfones," J. Am. Chem. Soc., vol. 72, 1950, pp. 3642-3646.
Henne et al., "Flourinated Acids," J. Am. Chem. Soc., vol. 69, 1947, pp. 281-283.
Henne et al., "Positive Bromine from Perfluorinated N-Bromoimides," J. Am. Chem. Soc., vol. 73, 1951, pp. 1103-1104.
Ward, "The Hyrolysis and Oxidation of α,ω-Bis(methylthio)polyfluoroalkanes," J. Org. Chem., vol. 30, 1965, pp. 3009-3011.
International Search Report issued in PCT/JP2009/005130, mailed Nov. 2, 2009. (with English-language translation).
International Preliminary Report on Patentability issued in International Application No. PCT/JP2009/005130 dated May 17, 2011 (with translation).

* cited by examiner

*Primary Examiner* — Porfirio Nazario Gonzalez
(74) *Attorney, Agent, or Firm* — Oliff & Berridge, PLC

(57) ABSTRACT

Provided is a method for producing a tetrafluoro nitrogen-containing heterocyclic compound such as tetrafluoropyrrolidine in good yield and at low cost. The method comprises the steps of: (A) reacting a compound represented by the formula (I) with fluorine gas to produce a tetrafluoro compound represented by the formula (II),
(B) converting the tetrafluoro derivative represented by the formula (II) to a compound represented by the formula (III), and
(C) reacting the compound represented by the formula (III) with an amine compound represented by the formula $NH_2R^9$ to produce a tetrafluoro nitrogen-containing heterocyclic compound represented by the formula (IV) or salt thereof.

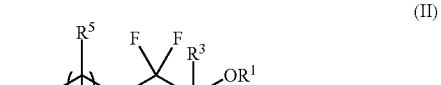

(I)

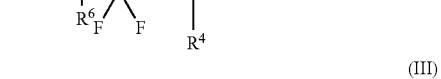

(II)

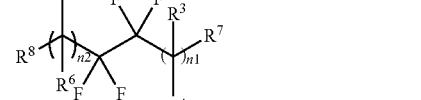

(III)

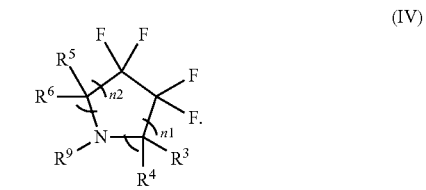

(IV)

3 Claims, No Drawings

METHOD FOR PRODUCING TETRAFLUORO COMPOUND

TECHNICAL FIELD

The present invention relates to a method for producing a tetrafluoro compound from an alkyne compound and a method for producing a tetrafluoro nitrogen-containing heterocyclic compound using the method.

This application claims priority to Japanese Patent Application No. 2008-260485, filed on Oct. 7, 2008, the disclosure of which is hereby incorporated herein by reference.

BACKGROUND ART

Conventionally, as a method for producing a tetrafluoro nitrogen-containing heterocyclic compound, for example, a method for producing tetrafluoropyrrolidine as follows is known (Patent Documents 1 and 2, Non-Patent Documents 1 to 4, and the like). However, these methods have required reduction using expensive LiAlH$_4$ or the like.

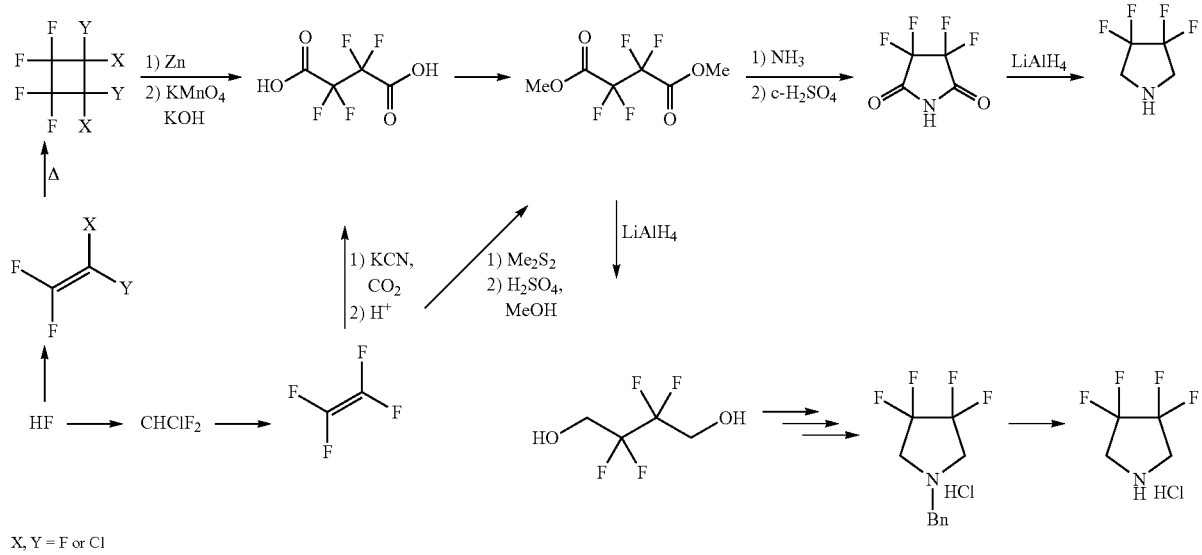

X, Y = F or Cl

Patent Document 1: WO03/101449
Patent Document 2: U.S. Pat. No. 4,474,700
Non-Patent Document 1: J. Am. Chem. Soc., 1950, 72:3642
Non-Patent Document 2: J. Am. Chem. Soc., 1947, 69:281
Non-Patent Document 3: J. Am. Chem. Soc., 1951, 73:1103
Non-Patent Document 4: J. Org. Chem. 1965, 30:3009

DISCLOSURE OF THE INVENTION

Object to be Solved by the Invention

An object of the present invention is to provide a method for producing a tetrafluoro nitrogen-containing heterocyclic compound such as tetrafluoropyrrolidine in good yield and at low cost.

Means to Solve the Object

As a result of intensive studies, the present inventors have discovered that the reaction of an alkyne compound represented by the formula (I) below with fluorine gas allows the production of a tetrafluoro compound represented by formula (II) in good yield, and have found that the use of the method in the production of a tetrafluoro nitrogen-containing heterocyclic compound such as tetrafluoropyrrolidine enables the production of the tetrafluoro nitrogen-containing heterocyclic compound at low cost and in good yield.

Thus, the present invention relates to [1] a method for producing a tetrafluoro compound represented by the formula (II):

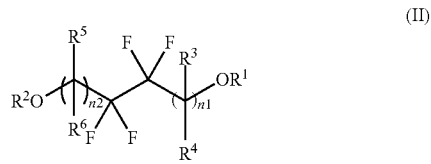

(II)

(wherein R$^1$ and R$^2$ each independently represent a hydrogen atom or a protective group for an OH group; R$^3$ to R$^6$ each independently represent a hydrogen atom or an alkyl group; and n1 and n2 each independently represent an integer of 1 or more) comprising reacting an alkyne compound represented by the formula (I):

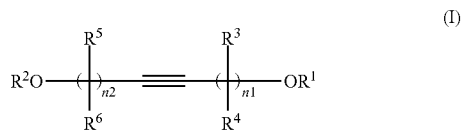

(I)

(wherein R$^1$ to R$^6$ and n1 and n2 are as defined above) with fluorine gas.

The present invention also relates to [2] a method for producing a tetrafluoro nitrogen-containing heterocyclic compound represented by the formula (IV) or a salt thereof:

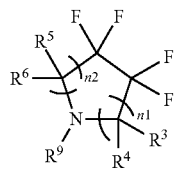

(wherein $R^3$ to $R^6$ each independently represent a hydrogen atom or an alkyl group; $R^9$ represents a hydrogen atom or a protective group for an amino group; and n1 and n2 each independently represent an integer of 1 or more) comprising the steps of (A) reacting a compound represented by the formula (I):

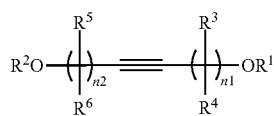

(wherein $R^1$ and $R^2$ each independently represent a hydrogen atom or a protective group for an OH group; and $R^3$ to $R^6$ and n1 and n2 are as defined above) with fluorine gas to produce a tetrafluoro compound represented by the formula (II):

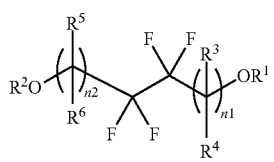

(wherein $R^1$ to $R^6$ and n1 and n2 are as defined above), (B) converting the tetrafluoro derivative represented by the formula (II) to a compound represented by the formula (III):

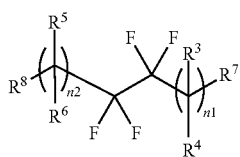

(wherein $R^3$ to $R^6$ are as defined above; and $R^7$ and $R^8$ each represent a leaving group), and (C) reacting the compound represented by the formula (III) with an amine compound represented by the formula $NH_2R^9$ (wherein $R^9$ is as defined above) to produce the tetrafluoro nitrogen-containing heterocyclic compound represented by the formula (IV).

Advantages of the Invention

According to the present invention, a tetrafluoro compound can be produced in good yield from an alkyne compound, and consequently a tetrafluoro nitrogen-containing heterocyclic compound can be produced at low cost and in good yield using the method.

MODE OF CARRYING OUT THE INVENTION

1. A method for producing a tetrafluoro compound represented by the formula (II).

An alkyne compound represented by the formula (I):

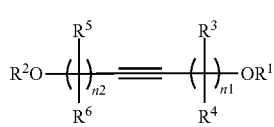

is reacted with fluorine gas to produce a tetrafluoro compound represented by the formula (II):

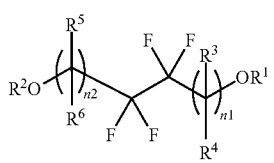

The alkyne compound represented by the formula (I) used for the present invention is as follows.

The substituents $R^1$ and $R^2$ each independently represent a hydrogen atom or a protective group for an OH group.

The protective group for an OH group may be a protective group generally used for protecting an OH group. Specific examples thereof include lower alkyl groups such as a methyl group; lower alkoxyalkyl groups such as a methoxymethyl group and an ethoxyethyl group; optionally substituted benzyl groups (examples of the substituent include a nitro group and lower alkoxy groups); lower alkoxycarbonyl groups; halogeno lower alkoxycarbonyl groups; optionally substituted benzyloxycarbonyl groups (examples of the substituent include a nitro group and lower alkoxy groups); acyl groups such as an acetyl group and a benzoyl group; a triphenylmethyl group; a tetrahydropyranyl group; a methanesulfonyl group; a p-toluenesulfonyl group; and tri-substituted silyl groups such as a trimethylsilyl group, a triethylsilyl group, a t-butyldimethylsilyl group, a triisopropylsilyl group, a dimethylhexylsilyl group and a t-butyldiphenylsilyl group.

$R^3$ to $R^6$ each independently represent a hydrogen atom or an alkyl group.

Examples of the alkyl group include a methyl group, an ethyl group, an n-propyl group, an i-propyl group, an n-butyl group, an s-butyl group, an i-butyl group, a t-butyl group, an n-pentyl group, an n-hexyl group, a nonyl group, an isononyl group, a decyl group, a dodecyl group, a tridecyl group, a tetradecyl group, a pentadecyl group, a hexadecyl group, a heptadecyl group, and an octadecyl group. Preferred is a C1-6 alkyl group.

n1 and n2 each independently represent an integer of 1 or more and are preferably 1 to 3.

Specific examples of the compound represented by the formula (I) include:

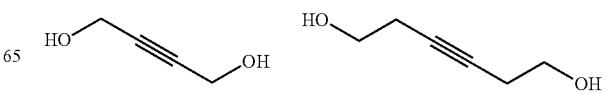

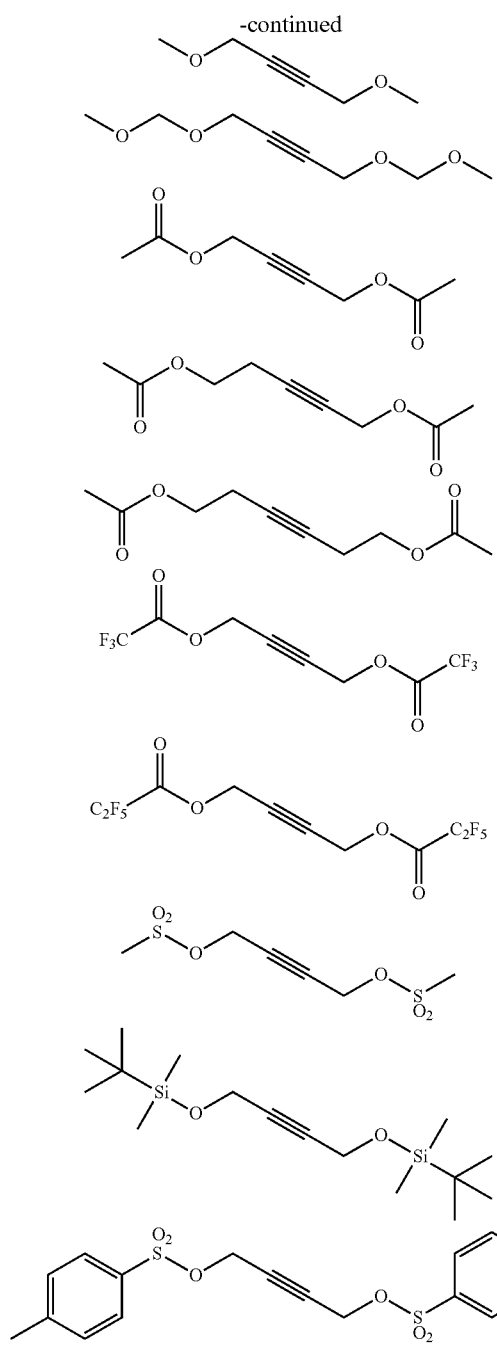

The fluorination reaction of an alkyne compound represented by the formula (I) in a solvent is carried out by fluorinating the alkyne compound represented by the formula (I) using fluorine gas. Typically, the alkyne compound represented by the formula (I) is added to the solvent, and the solution is reacted with the fluorine gas under stirring while bubbling with the gas.

The fluorine gas may be used directly or after dilution with an inert gas (nitrogen gas, helium gas, or the like). The amount thereof used is typically 1 to 10 mol, preferably 2 to 4 mol, based on 1 mol of the compound represented by the formula (I). The reaction temperature is typically −196 to 25° C., preferably −78 to 10° C. The reaction time is typically 1 to 10 hours, preferably 2 to 4 hours.

The solvent used for the fluorination is not particularly limited provided that the solvent is inert to fluorine gas.

Examples thereof include perfluoroalkanes such as perfluoropentane, perfluorohexane, perfluoroheptane, and perfluorooctane; perfluorocycloalkanes such as per fluorocyclopentane, perfluorocyclohexane, perfluorocycloheptane, and perfluorocyclooctane; the above in each of which some of the fluorine atoms are each replaced with another halogen atom (e.g., $CFCl_3$); perfluoroether; perfluoroalkylamines; trifluoroacetic acid; and acetonitrile. These solvents may be used singly or in mixtures of two or more thereof. Preferred examples thereof include mixed solvents such as a mixture of $CFCl_3$ and acetonitrile. The amount of the solvent used is 1 to 20 L, preferably 5 to 10 L, per mol of the alkyne compound represented by the formula (I).

For a compound having a protective group for an OH group, the protected OH group can be converted to an OH group by deprotection using a known method or the like.

Specific examples of the tetrafluoro compound represented by the formula (II) produced by the above method include:

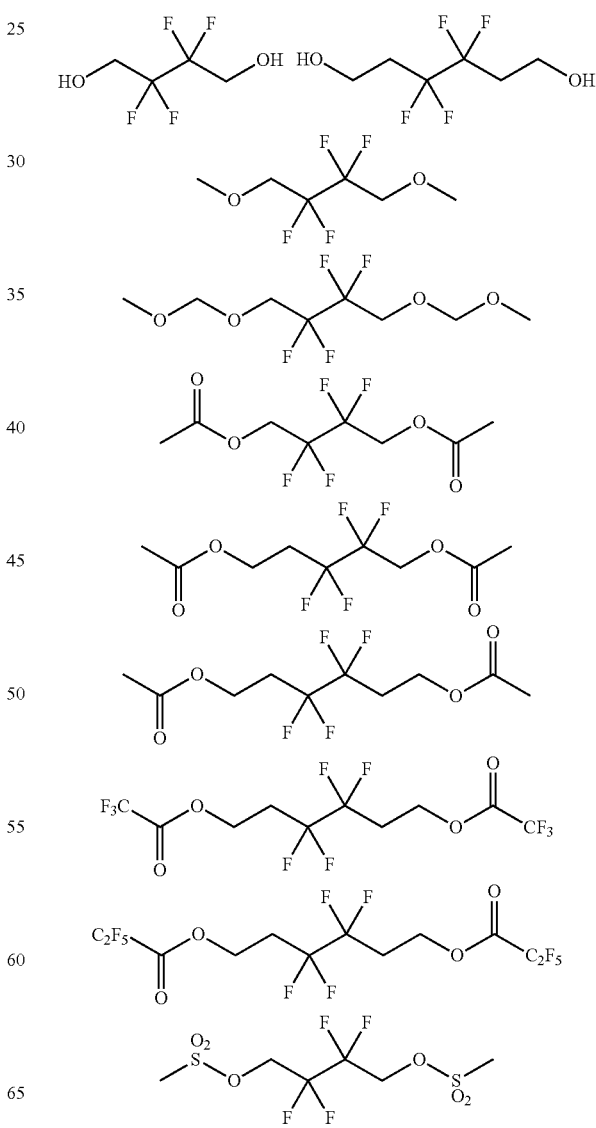

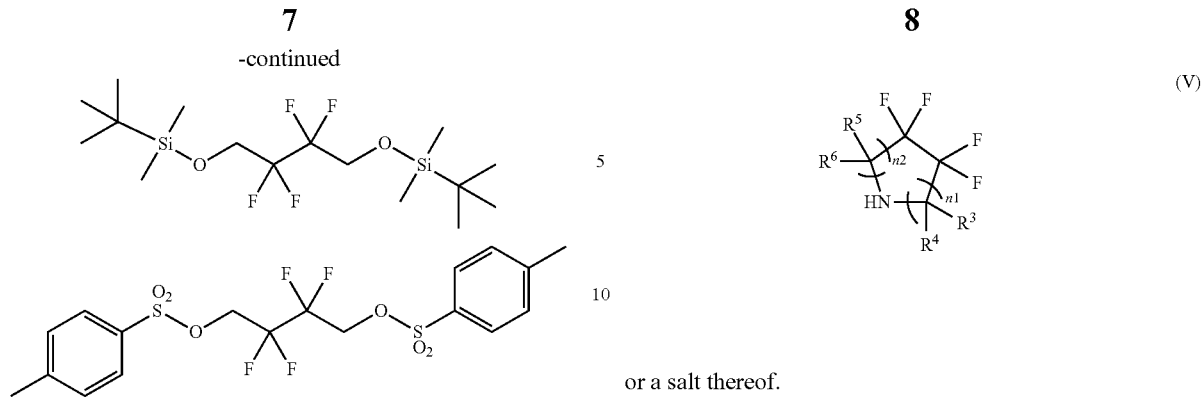

2. A method for producing a tetrafluoro nitrogen-containing heterocyclic compound represented by the formula (IV).

The method comprises the following steps.

Step 1

As shown in 1. above, a compound represented by the formula (I) is reacted with fluorine gas to produce a tetrafluoro compound represented by the formula (II). When the tetrafluoro compound represented by the formula (II) has a protective group for an OH group, the protected OH group may be converted to an OH group by deprotection in step 1.

Step 2

The tetrafluoro derivative represented by the formula (II) is converted to a compound represented by the formula (III):

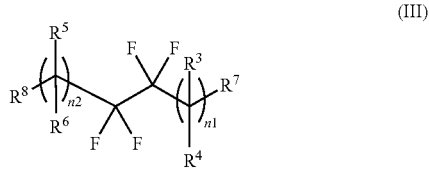
(III)

Step 3

The compound represented by the formula (III) is reacted with an amine compound represented by the formula $NH_2R^9$ to produce a tetrafluoro nitrogen-containing heterocyclic compound represented by the formula (IV):

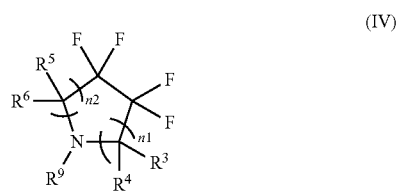
(IV)

or a salt thereof.

Step 4

When $R^9$ in the formula (IV) is a protective group for an amino group, the compound represented by the formula (IV) can also be further deprotected in a solvent after step 3 to produce a compound represented by the formula (V):

(V)

or a salt thereof.

(Description of Step 2)

In the formula (III) obtained in step 2, $R^7$ and $R^8$ are each a group that can leave in response to a nucleophilic reagent, including halogen atoms such as a chlorine atom and a bromine atom; and organic sulfonyloxy groups such as a methanesulfonyloxy group, an ethanesulfonyloxy group, a trifluoromethanesulfonyloxy group, a benzenesulfonyloxy group, and a p-toluenesulfonyloxy group.

A compound represented by the formula (II), directly when $R^1$ and $R^2$ are each a hydrogen atom, or after conversion thereof to OH groups by hydrolysis when $R^1$ and $R^2$ are each a protective group for an OH group, can be reacted with a reagent such as thionyl chloride, methanesulfonyl chloride, 4-toluenesulfonyl chloride or trifluoromethanesulfonic anhydride in a solvent to provide a compound represented by the formula (III).

The amount of the reagent used in the conversion to leaving groups is typically 2 to 10 mol, preferably 2 to 3 mol, based on 1 mol of the compound represented by the formula (II). The reaction temperature is typically −78 to 200° C., preferably −5 to 20° C. The reaction time is typically 1 to 24 hours, preferably 2 to 4 hours.

Examples of the solvent that can be used in the conversion to leaving groups include tetrahydrofuran, acetonitrile, toluene, chloroform, and dichloromethane. These solvents may be used singly or in mixtures of two or more thereof. The amount of the solvent used is 1 to 10 L, preferably 1 to 3 L, per mol of the tetrafluoro compound represented by the formula (II).

(Description of Step 3)

In the formula (IV) obtained in step 3, $R^3$ to $R^6$ and n1 and n2 are as defined in the above formula (I). $R^9$ is a hydrogen atom or a protective group for an amino group.

The protective group for an amino group of $R^9$ may be a protective group generally used for protecting N. Specific examples thereof include a t-butyl group; an allyl group; tri-substituted silyl groups such as a trimethylsilyl group, a triethylsilyl group, a t-butyldimethylsilyl group, a triisopropylsilyl group, a dimethylhexylsilyl group, and a t-butyldiphenylsilyl group; optionally substituted benzyl groups (examples of the substituent include a nitro group and lower alkoxy groups); lower alkoxycarbonyl groups such as a t-butoxycarbonyl group; halogeno lower alkoxycarbonyl groups; optionally substituted benzyloxycarbonyl groups (examples of the substituent include a nitro group and lower alkoxy groups); and acyl groups such as an acetyl group and a benzoyl group.

Examples of the tetrafluoro nitrogen-containing heterocyclic compound represented by the formula (IV) include the following.

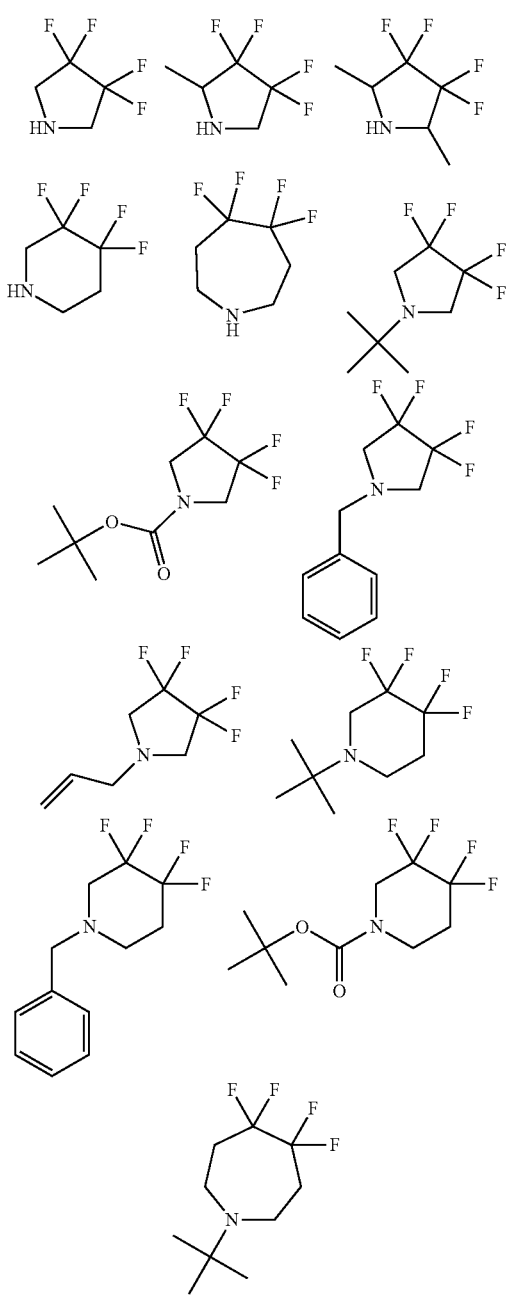

Examples of the salt of a tetrafluoro nitrogen-containing heterocyclic compound represented by the formula (IV) include salts with inorganic acids such as hydrochloric acid, hydrobromic acid, hydroiodic acid, nitric acid, sulfuric acid, and phosphoric acid and salts with organic acids such as acetic acid, fumaric acid, maleic acid, succinic acid, citric acid, and tartaric acid.

A compound represented by the formula (III) can be reacted with a primary amine compound represented by the formula $NH_2R^9$ ($R^9$ represents a hydrogen atom or a protective group for an amino group) to provide a tetrafluoro nitrogen-containing heterocyclic compound represented by the formula (IV).

Examples of the primary amine compound represented by the formula $NH_2R^9$ include t-butylamine, allylamine, trimethylsilylamine, benzylamine, t-butoxycarbonylamine, and benzoylamine.

The amount of the primary amine compound used is typically 1 to 10 mol, preferably 1 to 3 mol, based on 1 mol of the compound represented by the formula (III). The reaction temperature is typically 0 to 200° C., preferably 0 to 80° C. The reaction time is typically 1 to 24 hours, preferably 5 to 20 hours.

Examples of the solvent which can be used include chloroform and ethanol. These solvents may be used singly or in mixtures of two or more thereof. The amount of the solvent used is 1 to 10 L, preferably 1 to 3 L, based on 1 mol of the tetrafluoro compound represented by the formula (II).

(Description of Step 4)

For the deprotection of a compound represented by the formula (IV), a suitable method may be properly selected depending on the type of the protective group. Deprotection methods include methods as described in PROTECTIVE GROUPS IN ORGANIC SYNTHESIS 2nd. Ed. For example, when the protective group is a t-butyl group, a t-butoxycarbonyl group, or the like, the compound may be treated with an acid such as trifluoroacetic acid, hydrochloric acid, sulfuric acid, p-toluenesulfonic acid or methanesulfonic acid. When the protective group is a benzyl group or the like, the compound may be subjected to hydrogenolysis in the presence of a palladium catalyst or the like.

After the end of reaction, a desired product can be isolated by a usual after-treatment operation and, if desired, purification using a known conventional purifying means such as distillation, recrystallization or column chromatography.

EXAMPLES

The present invention will be more specifically described below with reference to Examples. However, these Examples are not intended to limit the technical scope of the present invention. In the following Examples, A % indicates area ratio in percent.

Example 1

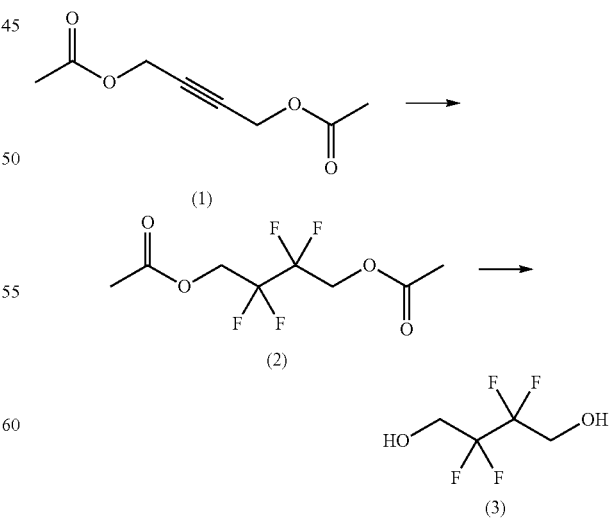

In a reaction vessel having a cooler and a gas blowing port were placed 0.94 g (5.5 mmol) of the compound (1) and 30 ml of CFCl$_3$. The reaction vessel was cooled to −78° C. and then purged with nitrogen, into which N$_2$ gas containing 10% F$_2$ was subsequently blown at a rate of 50 ml/min for 55 minutes. Thereafter, 10 ml of acetonitrile was added thereto, into which N$_2$ gas containing 10% F$_2$ was then blown at a rate of 50 ml/min for 55 minutes while the temperature was adjusted to 5 to 10° C. After the end of fluorination reaction, the reaction solution was purged with nitrogen to remove excess fluorine, followed by pouring the reaction solution into sodium bicarbonate. Subsequently, the residue was extracted with methylene chloride, and the organic layer was washed with water and then dried over magnesium sulfate, followed by distilling off the solvent to provide 1.29 g of a crude product of the compound (2)

In addition, 5 ml of dilute sulfuric acid was added to 1.29 g of the crude product of the compound (2), which was then hydrolyzed while heated under reflux. After the end of reaction, water and ether were added and the organic layer was washed with saturated saline and dried over magnesium sulfate. The solvent was distilled off to provide 0.48 g of a crude product of the compound (3) (2,2,3,3-tetrafluorobutanediol). The content of the compound (3) in the composition was found to be 64% using gas chromatography.

Example 2

To a methylene chloride solution of 19.45 g (120 mmol; mmol in terms of pure content) of the crude product containing the compound (3) obtained in Example 1 and 23.7 g (300 mmol) of pyridine was dropwise added 72.8 g (257 mmol) of trifluoromethanesulfonic anhydride in the range of −5 to 5° C., which was then reacted at the same temperature for one hour and further at room temperature for 1 hour. The reaction solution was then washed with water and dried with magnesium sulfate, followed by distilling off the solvent to provide a crude product containing 2,2,3,3-tetrafluoro-1,4-bis(trifluoromethanesulfonyloxy)-butane, a desired product.

An ethanol solution of the residue crude product, 12.8 g (120 mmol) of benzylamine and 30.4 g (300 mmol) of triethylamine was refluxed for 20 hours. After cooling the solution to room temperature, the solvent was distilled off, and ether was added thereto. The organic layer was washed with alkali and saturated saline and then dried with magnesium sulfate.

Magnesium sulfate was filtered off from the ether solution, and hydrogen chloride gas was blown into the residue ether solution in the range of 0° C. to room temperature for 1 hour.

Thereafter, nitrogen gas was blown thereinto to remove the excess hydrogen chloride. The precipitated crystal was filtered and washed with ether to provide 16.9 g (yield: 82% in terms of pure content) of desired 3,3,4,4-tetrafluoro-1-benzyl-pyrrolidine hydrochloride.

An ethanol solution of 16.9 g of the residue 3,3,4,4-tetrafluoro-1-benzyl-pyrrolidine hydrochloride and 1.8 g of 10% Pd/C was stirred at room temperature for 3 hours in a manner of contacting hydrogen gas under ordinary pressure. After filtration, the solvent was distilled off to provide 11 g (yield: 98%) of desired 3,3,4,4-tetrafluoro-pyrrolidine hydrochloride.

Example 3

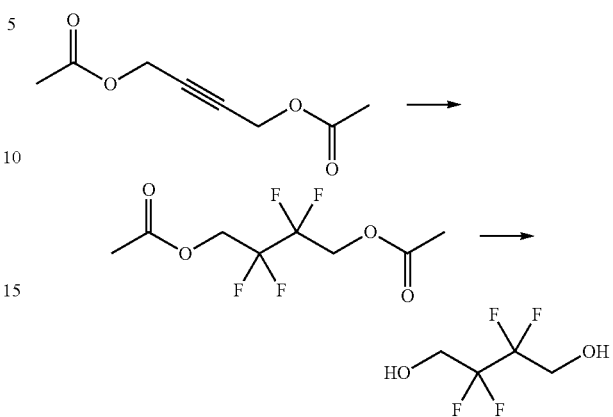

0.94 g (5.5 mmol) of 2-butyne-1,4-diol diacetate was weighed in a reaction vessel having a cooler and a gas blowing port and dissolved in a mixed solvent of 10 ml of acetonitrile and 30 ml of trichlorofluoromethane. The solution was cooled to −50° C. while nitrogen (50 ml/min) was blown thereinto and thereby purged with nitrogen for 15 minutes. Thereafter, fluorine gas diluted to 10% with nitrogen was blown thereinto at a rate of 50 ml/min for 123 minutes. After the end of fluorination reaction, nitrogen (50 ml/min) was blown at −50° C. into the reaction solution for 15 minutes to remove excess fluorine, and the reaction solution was added to saturated sodium bicarbonate water. Subsequently, the residue was extracted three times with methylene chloride, and the organic layer was washed with water and then dried over magnesium sulfate. After filtering off the dehydrating agent, the solvent was distilled off under reduced pressure to provide 1.54 g of a crude product of 2,2,3,3-tetrafluorobutane-1,4-diol diacetate. 5 ml of dilute sulfuric acid was added to the crude product, which was then heated under reflux for 3 hours. The reaction solution was cooled and then added to saturated sodium bicarbonate water cooled with ice. Then, ethyl acetate was added thereto, and insoluble matter was filtered off with celite. The filtrate was separated, the aqueous layer was then extracted two times with ethyl acetate, and the organic layer was washed with saturated saline and then dried over magnesium sulfate. After filtering off the dehydrating agent, the solvent was distilled off under reduced pressure to provide 0.22 g of a crude product of 2,2,3,3-tetrafluorobutane-1,4-diol.

Example 4

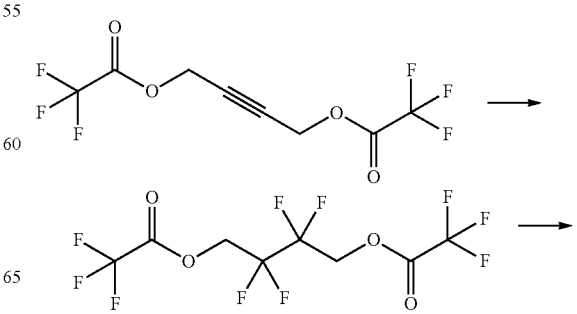

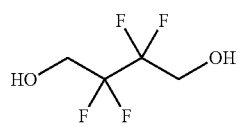

Using 1.53 g of 2-butyne-1,4-diol bis(2,2,2-trifluoroacetate) in place of 2-butyne-1,4-diol diacetate, 0.18 g of a crude product of 2,2,3,3-tetrafluorobutane-1,4-diol was obtained in the same condition as in Example 1.

Example 5

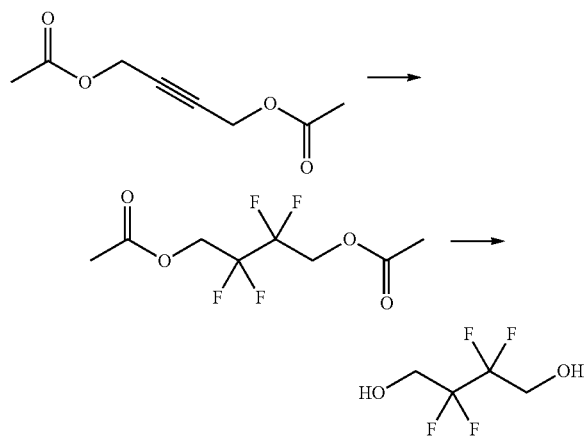

0.95 g (5.6 mmol) of 2-butyne-1,4-diol diacetate was weighed in a reaction vessel having a cooler and a gas blowing port and dissolved in a mixed solvent of 10 ml of acetonitrile and 30 ml of trichlorofluoromethane. The solution was cooled to −50° C. while nitrogen (50 ml/min) was blown thereinto and thereby purged with nitrogen for 15 minutes. Thereafter, fluorine gas diluted to 10% with nitrogen was blown thereinto at a rate of 50 ml/min for 123 minutes. After the end of fluorination reaction, nitrogen (50 ml/min) was blown at −50° C. into the reaction solution for 1 hour to remove excess fluorine. The solvent was distilled off under reduced pressure to provide 1.67 g of a crude product of 2,2,3,3-tetrafluorobutane-1,4-diol diacetate. 5 ml of dilute sulfuric acid was added to the crude product, which was then heated under reflux for 3 hours. The reaction solution was cooled and then added to ethyl acetate and sodium bicarbonate cooled with ice. Insoluble matter was filtered off with celite, and the organic layer was then dried over magnesium sulfate. After filtering off the dehydrating agent, the solvent was distilled off under reduced pressure to provide 0.33 g of a crude product of 2,2,3,3-tetrafluorobutane-1,4-diol.

Example 6

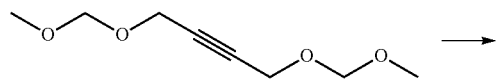

0.96 g (5.5 mmol) of 1,4-bis(methoxymethoxy)-2-butyne was weighed in a reaction vessel having a cooler and a gas blowing port and dissolved in a mixed solvent of 10 ml of acetonitrile and 30 ml of trichlorofluoromethane. The solution was cooled to −50° C. while nitrogen (50 ml/min) was blown thereinto and thereby purged with nitrogen for 15 minutes. Thereafter, fluorine gas diluted to 10% with nitrogen was blown thereinto at a rate of 50 ml/min for 123 minutes. After the end of fluorination reaction, nitrogen (50 ml/min) was blown at −50° C. into the reaction solution for 15 minutes to remove excess fluorine, and the reaction solution was added to saturated sodium bicarbonate water. Subsequently, the residue was extracted three times with ethyl acetate, and the organic layer was washed with water and then dried over magnesium sulfate. After filtering off the dehydrating agent, the solvent was distilled off under reduced pressure to provide 1.41 g of a crude product of 1,4-bis(methoxymethoxy)-2,2,3,3-tetrafluorobutane. From analysis using gas chromatography, the area ratio in percent of 1,4-bis(methoxymethoxy)-2,2,3,3-tetrafluorobutane in the crude product was found to be 26 A %.

Example 6

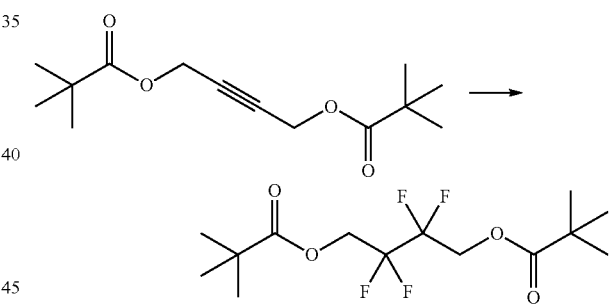

Using 1.40 g of 1,4-bis(pivaloyloxy)-2-butyne in place of 1,4-bis(methoxymethoxy)-2-butyne, 2.11 g of a crude product of 1,4-bis(pivaloyloxy)-2,2,3,3-tetrafluorobutane was obtained in the same condition as in Example 4. From analysis using gas chromatography, the area ratio in percent of 1,4-bis(pivaloyloxy)-2,2,3,3-tetrafluorobutane in the crude product was found to be 18 A %.

Example 7

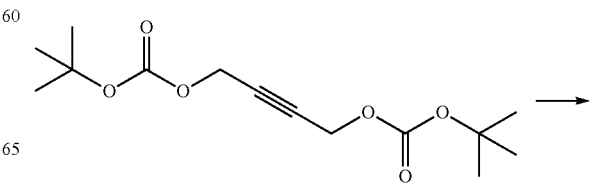

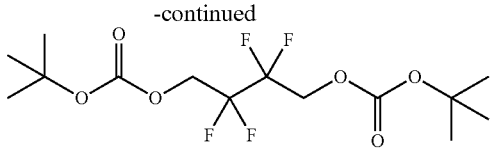

Using 1.57 g of 1,4-bis(t-butoxycarbonyloxy)-2-butyne in place of 1,4-bis(methoxymethoxy)-2-butyne, 2.29 g of a crude product of 1,4-bis(t-butoxycarbonyloxy)-2,2,3,3-tetrafluorobutane was obtained in the same condition as in Example 4. From analysis using gas chromatography, the area ratio in percent of 1,4-bis(t-butoxycarbonyloxy)-2,2,3,3-tetrafluorobutane in the crude product was found to be 18 A %.

Example 8

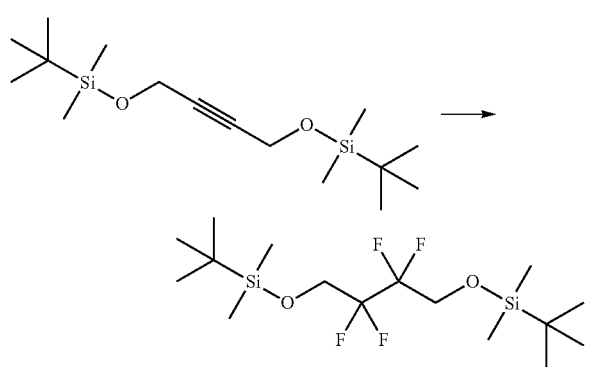

Using 1.73 g of 1,4-bis(t-butyldimethylsilyloxy)-2-butyne in place of 1,4-bis(methoxymethoxy)-2-butyne, 2.49 g of a crude product of 1,4-bis(t-butyldimethylsilyloxy)-2,2,3,3-tetrafluorobutane was obtained in the same condition as in Example 4, From analysis using gas chromatography, the area ratio in percent of 1,4-bis(t-butyldimethylsilyloxy)-2,2,3,3-tetrafluorobutane in the crude product was found to be 25 A %.

Example 9

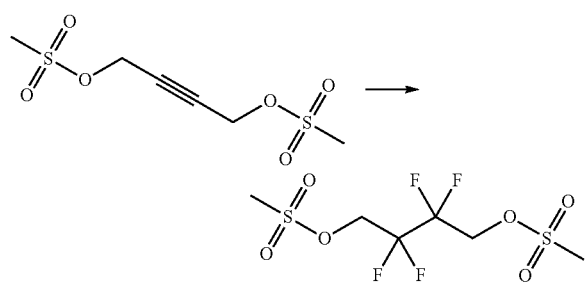

Using 1.30 g of 1,4-bis(methylsulfonyloxy)-2-butyne in place of 1,4-bis(methoxymethoxy)-2-butyne, 1.97 g of a crude product of 1,4-bis(methylsulfonyloxy)-2,2,3,3-tetrafluorobutane was obtained in the same condition as in Example 4. From analysis using gas chromatography, the area ratio in percent of 1,4-bis(methylsulfonyloxy)-2,2,3,3-tetrafluorobutane in the crude product was found to be 7 A %.

Example 10

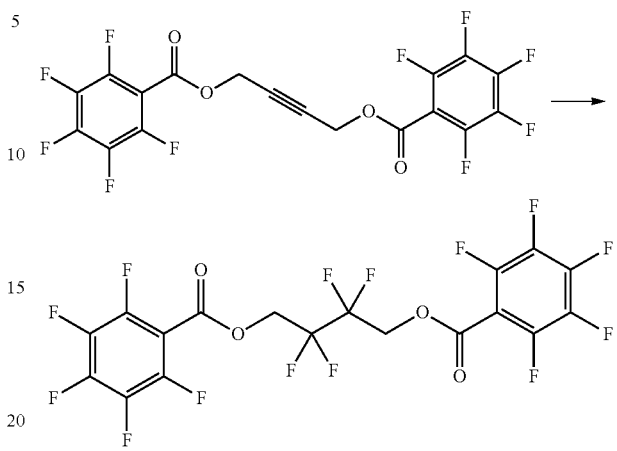

Using 2.60 g of 1,4-bis(perfluorobenzoyloxy)-2-butyne in place of 1,4-bis(methoxymethoxy)-2-butyne, 3.26 g of a crude product of 1,4-bis(perfluorobenzoyloxy)-2,2,3,3-tetrafluorobutane was obtained in the same condition as in Example 4. From analysis using gas chromatography, the area ratio in percent of 1,4-bis(perfluorobenzoyloxy)-2,2,3,3-tetrafluorobutane in the crude product was found to be 27 A %.

Example 11

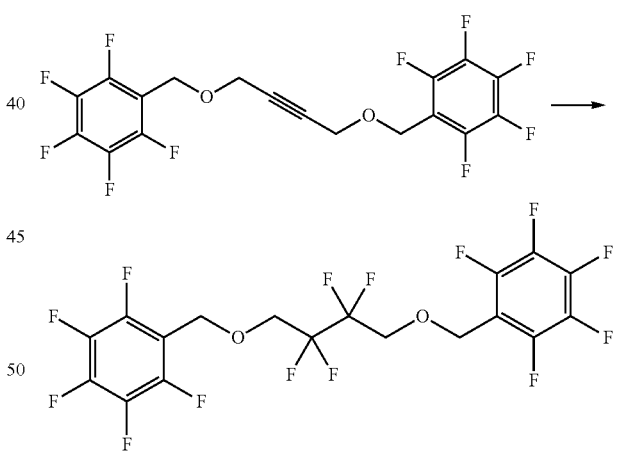

Using 2.35 g of 1,4-bis(perfluorobenzyloxy)-2-butyne in place of 1,4-bis(methoxymethoxy)-2-butyne, 3.06 g of a crude product of 1,4-bis(perfluorobenzyloxy)-2,2,3,3-tetrafluorobutane was obtained in the same condition as in Example 4. From analysis using gas chromatography, the area ratio in percent of 1,4-bis(perfluorobenzyloxy)-2,2,3,3-tetrafluorobutane in the crude product was found to be 19 A %.

The invention claimed is:

1. A method for producing a tetrafluoro compound represented by formula (II):

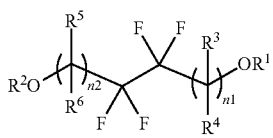

(II)

wherein:
R$^1$ and R$^2$ each independently represent lower alkoxyalkyl group, an optionally substituted benzyl group, a lower alkoxycarbonyl group, an acyl group, or a tri-substituted silyl group;
R$^3$ to R$^6$ represent a hydrogen atom; and
n1 and n2 each independently represent an integer of 1;
the method comprising:
reacting an alkyne compound represented by formula (I):

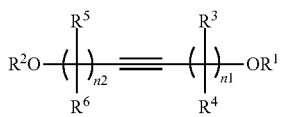

(I)

wherein R$^1$ to R$^6$ and n1 and n2 are as defined above, with fluorine gas.

2. A method for producing a tetrafluoro nitrogen-containing heterocyclic compound represented by formula (IV) or a salt thereof:

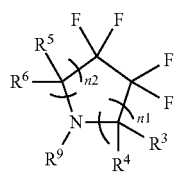

(IV)

wherein
R$^3$ to R$^6$ represent a hydrogen atom;
R$^9$ represents a hydrogen atom or a protective group for an amino group; and
n1 and n2 each independently represent an integer of 1;
comprising the steps of:
(A) reacting a compound represented by formula (I):

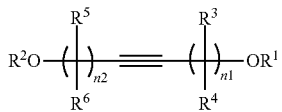

(I)

wherein:
R$^1$ and R$^2$ each independently represent a lower alkoxyalkyl group, an optionally substituted benzyl group, a lower alkoxycarbonyl group, an acyl group, or a tri-substituted silyl group; and
R$^3$ to R$^6$ and n1 and n2 are as defined above,
with fluorine gas to produce a tetrafluoro compound represented by formula (II):

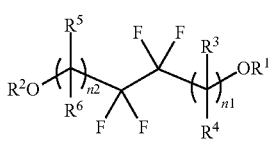

(II)

wherein R$^1$ to R$^6$ and n1 and n2 are as defined above,
(B) converting the tetrafluoro derivative represented by formula (II) to a compound represented by formula (III):

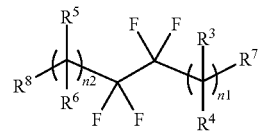

(III)

wherein:
R$^3$ to R$^6$ are as defined above; and
R$^7$ and R$^8$ each represent a leaving group, and
(C) reacting the compound represented by formula (III) with an amine compound represented by NH$_2$R$^9$, wherein R$^9$ is as defined above, to produce the tetrafluoro nitrogen-containing heterocyclic compound represented by formula (IV).

3. The method for producing a tetrafluoro nitrogen-containing heterocyclic compound or a salt thereof according to claim 2, further comprising the step of deprotecting the compound represented by formula (IV), wherein R9 represents a protective group for an amino group, to produce a compound represented by formula (V):

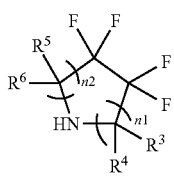

(V)

wherein R$^3$ to R$^6$ and n1 and n2 are as defined above.

* * * * *